(12) United States Patent
Baek et al.

(10) Patent No.: US 8,450,234 B2
(45) Date of Patent: May 28, 2013

(54) METHOD OF PRODUCING A CATALYST USED FOR SYNTHESIZING DIMETHYLETHER FROM A SYNTHESIS GAS CONTAINING CARBON DIOXIDE

(75) Inventors: Young Soon Baek, Incheon-si (KR); Won Jun Cho, Uijeongbu-si (KR); Yun Bin Yan, Incheon-si (KR); Yong Gi Mo, Incheon-si (KR); Kyung Hae Lee, Bucheon-si (KR); Eun Mee Jang, Seoul (KR)

(73) Assignee: Korea Gas Corporation, Seongnam-Si (KR)

(*) Notice: Subject to any disclaimer, the term of this patent is extended or adjusted under 35 U.S.C. 154(b) by 1399 days.

(21) Appl. No.: 11/678,092

(22) Filed: Feb. 23, 2007

(65) Prior Publication Data

US 2008/0125311 A1 May 29, 2008

(30) Foreign Application Priority Data

Nov. 28, 2006 (KR) .................. 10-2006-0118385

(51) Int. Cl.
*B01J 27/25* (2006.01)
*C07C 1/04* (2006.01)

(52) U.S. Cl.
CPC ............... *B01J 27/25* (2013.01); *C07C 1/048* (2013.01); *C07C 2523/54* (2013.01)
USPC .......................... 502/201; 518/712

(58) Field of Classification Search
None
See application file for complete search history.

(56) References Cited

U.S. PATENT DOCUMENTS

| 4,098,809 A | 7/1978 | Pagani |
| 4,177,167 A | 12/1979 | Manara et al. |
| 4,328,129 A | 5/1982 | Huang |
| 4,375,424 A | 3/1983 | Slaugh |
| 4,417,000 A | 11/1983 | Slaugh et al. |
| 4,595,785 A | 6/1986 | Brake |
| 5,254,520 A * | 10/1993 | Sofianos .............. 502/307 |
| 5,254,596 A | 10/1993 | Irick, Jr. et al. |
| 5,753,716 A * | 5/1998 | Peng et al. ............ 518/700 |
| 6,069,180 A * | 5/2000 | Peng et al. ............ 518/700 |
| 6,248,795 B1 * | 6/2001 | Jun et al. ............. 518/713 |

FOREIGN PATENT DOCUMENTS

| CN | 1356163 | 7/2002 |
| DE | 291937 | 9/1912 |
| DE | 2362944 | 12/1973 |
| DE | 2757788 | 12/1977 |
| DE | 3201155 | 2/1981 |
| DE | 3118620 | 5/1981 |
| DE | 3220547 | 6/1981 |
| DK | 603187 | 2/1989 |
| DK | 216989 | 8/1991 |
| EP | 0164156 | 8/1988 |
| EP | 0409086 A1 | 1/1991 |
| GB | 1398696 | 12/1972 |
| GB | 2093365 | 9/1982 |
| GB | 2097382 | 11/1982 |
| GB | 2099327 | 12/1982 |
| JP | 2003334445 | 11/2003 |
| JP | 200499489 | 4/2004 |
| KR | 20000002477 | 1/2000 |

OTHER PUBLICATIONS

Computer generated translation of JP 2001070793A, claims and abstract published Mar. 2001.*
"IDS Document English Abstract"—including English abstracts for foreign references cited above, Jun. 2007.

* cited by examiner

*Primary Examiner* — Rosalynd Keys
(74) *Attorney, Agent, or Firm* — Kile Park Reed & Houtteman PLLC

(57) ABSTRACT

The present invention relates to a catalyst used for producing dimethylether, a method of producing the same, and a method of producing dimethylether using the same. More particularly, the present invention relates to a catalyst used for producing dimethylether comprising a methanol synthesis catalyst produced by adding one or more promoters to a main catalyst comprised of a Cu—Zn—Al metal component and a dehydration catalyst formed by mixing Aluminum Phosphate (AlPO$_4$) with gamma alumina, a method of producing the same, and a method of producing dimethylether using the same, wherein a ratio of the main catalyst to the promoter in the methanol synthesis catalyst is in a range of 99/1 to 95/5, and a mixing ratio of the methanol synthesis catalyst to the dehydration catalyst is in a range of 60/40 to 70/30.

5 Claims, 1 Drawing Sheet

METHOD OF PRODUCING A CATALYST USED FOR SYNTHESIZING DIMETHYLETHER FROM A SYNTHESIS GAS CONTAINING CARBON DIOXIDE

BACKGROUND OF THE INVENTION

1. Field of the Invention

The present invention relates to a catalyst used for producing dimethylether, a method of producing the same, and a method of producing dimethylether using the same, and more particularly, to a catalyst used for producing dimethylether, a method of producing the same, and a method of producing dimethylether using the same, capable of increasing a conversion rate of carbon monoxide and a production amount of dimethylether by mixing a methanol synthesis catalyst which is produced by adding one or more promoters to a CuO—ZnO—$Al_2O_3$-based main catalyst in order to increase a degree of dispersion of a Cu metal acting as a catalytic active point, with a dehydration catalyst in which Aluminum Phosphate is mixed with gamma alumina, when dimethylether is produced by synthesizing methanol from a synthesis gas containing hydrogen, carbon monoxide, and carbon dioxide and by dehydrating the methanol.

2. Description of the Related Art

Dimethylether is an oxygen-containing compound which has been recently found. Physical and chemical characteristics of dimethylether are similar to those of a liquified petroleum gas (LPG). However, the dimethylether is rather superior to LPG in several aspects. Therefore, the dimethylether can be used as aerosol propellants, a substitute for a diesel fuel, and an intermediate material in a chemical reaction.

As a representative method of synthesizing dimethylether, there is a method of reacting methanol with a strong sulfuric acid catalyst. However, this method has many problems in cost and stability. Namely, high cost is required to reproduce sulfuric acid, and explosion may occur by reacting sulfuric acid with water generated during reaction due to a characteristic of sulfuric acid. As a method capable of overcoming such problems as well as producing the dimethylether in industrial scale, there is a method of collecting the dimethylether in high purity required in aerosol field, by dehydrating methanol using a solid acid dehydration catalyst in a fixed bed reactor and distilling a product thereof.

However, in order to use the dimethylether as the substitute for the diesel fuel, the dimethylether needs to be commercially supplied at a low price. The dimethylether obtained through a dehydration reaction of methanol under the presence of an acid catalyst is formed by synthesizing the methanol from a synthesis gas and performing an acid catalyst reaction. Therefore, the dimethylether is very much higher in price than methanol. In addition, the methanol synthesis reaction is limited thermodynamically to a conversion rate in characteristic thereof.

In order to solve this problem, there is developed a method of synthesizing dimethylether directly from a synthesis gas using a mixed catalyst in which a methanol synthesis catalyst is mixed with an acid catalyst of a dehydration reaction. In the process of synthesizing the dimethylether using the mixed catalyst, the methanol is removed through the dehydration reaction, and water obtained in the process of the dehydration reaction is removed through a water reaction. Therefore, the characteristic of the catalyst is improved, and the conversion rate of carbon monoxide and the yield of dimethylether increase. That is, in the process of reaction of synthesizing the dimethylether directly from the synthesis gas, three reactions (the methanol synthesis reaction, the water gas shift reaction, and the dehydration reaction) are performed simultaneously in the mixed catalyst. The reactions that are performed simultaneously compensates for the problems of the other reactions to solve the problems chemically.

Many producing methods including a method of synthesizing the dimethylether directly from hydrogen and carbon oxide are disclosed in documents. The methods of producing the dimethylether directly from a synthesis gas containing hydrogen, carbon monoxide, and carbon dioxide using a methanol catalyst and a dehydration catalyst together in a fixed bed reactor are disclosed in German Patent No. 291,937, U.S. Pat. Nos. 5,254,596, 4,417,000, 4,177,167, 4,375,424, and 4,098,809, European Patents Nos. 164,156 and 409,086, UK Patents Nos. 2,093,365, 2,097,382, and 2,099,327, German Patents Nos. 3,220,547, 3,201,155, 3,118,620, 2,757, 788, and 2,362,944, Danish Patents Nos. 6031/87, and 2169/89, Japanese Patents Nos. 04334445 and 0399489, and Chinese Patent Nos. 1356163.

As a catalyst of the methanol synthesis reaction, a three-phase catalyst is mainly used. In the three-phase catalyst, Cu metal is used as a main material, and materials such as zinc, alumina, chromium, titanium, and the like are used to change a support, and oxides mixed at the several ratio is used. The catalyst represents an activity with respect to not only a water reaction but also an inverse water reaction. In addition, an acid catalyst is used mainly in the dehydration reaction of methanol. As an example of the acid catalyst, there are alumina, zeolite, silica/alumina, metallic salt, an ion exchange resin, and a mixed metal oxide. In dimethylether synthesis process using the mixed catalyst, a characteristic of a promoter in the mixed catalyst has great influence on a conversion rate of a synthesis gas and a selectivity and a yield of a product.

Recently, instead of a method of using by mixing physically such a promoter and a methanol synthesis catalyst, there is proposed a method of using a catalyst in which effective components are synthesized through co-precipitation. For example, in U.S. Pat. No. 4,328,129, a catalyst in which rhodium of 3 wt % and molybdenum of 6.5 wt % are immersed in gamma alumina support is used. Under the condition of 230 psi and 220 to 280° C., when reactant composition is $CO:H_2=1:2$, a conversion rate of synthesis gas into dimethylether and methanol was obtained in a range of 27.1 to 57.3% on the basis of carbon monoxide. When reactant composition is $CO:H_2=1:1$, the conversion rate was obtained in a range of 28.2 to 42.2%.

In addition, in U.S. Pat. No. 4,375,424, gamma alumina was immersed in a solution of copper nitrate and zinc nitrate to produce a catalyst. In this case, under the condition of 1700 psi, 100 to 275° C., 3000 GHSV (Gas Hourly Space Velocity), and $CO:H_2=1:1$ of reactant composition, the conversion rate of CO was obtained in a range of 5.8 to 70.4%, and the conversion rate of dimethylether were obtained in a range of 2.8 to 94.4%.

Meanwhile, techniques for improving characteristics of an acid catalyst used in synthesis of dimethylether have actively researched. In addition, techniques for increasing the yield and the selectivity of dimethylether by immersing an active element in gamma alumina have been tried. For example, U.S. Pat. No. 4,595,785 discloses that the dehydration reaction of methanol is performed under the condition of 1034 kPa, 400° C. using catalyst in which 1% titania is immersed in gamma alumina. As a result, a condensate product containing 57.5% dimethylether, 20% of methanol, and 22.5% water was obtained. Korean Patent Application Publication No. 2000-0002477 discloses that an acid catalyst reformed by formaldehyde is used to synthesize dimethylether from synthesis gas so as to obtain a high conversion rate of carbon monoxide and the selectivity and the yield of dimethylether. However, in the process, alkali component with formaldehyde are used, so that the conversion rate of carbon monoxide is still low.

SUMMARY OF THE INVENTION

The present invention provides a mixed catalyst used for producing dimethylether capable of producing selectively dimethylether having a high conversion rate of carbon monoxide from a mixed gas containing hydrogen, carbon monoxide, and carbon dioxide.

The present invention also provides a method of producing a mixed catalyst used for producing dimethylether.

The present invention also provides a method of producing dimethylether using a mixed catalyst used for producing dimethylether.

According to an aspect of the present invention, there is provided a mixed catalyst used for producing dimethylether comprising a methanol synthesis catalyst and a dehydration catalyst. The methanol synthesis catalyst is produced from a sodium carbonate solution and a metal nitrate solution formed by adding a promoter including at least one selected from Mg, Zr, Ga, Ca, or the oxide thereof to a main catalyst. The main catalyst is a solution where a copper nitrate solution, a zinc nitrate solution, and an aluminum nitrate solution are mixed. The dehydration catalyst is formed by mixing aluminum phosphate ($AlPO_4$) with gamma alumina. A ratio of the main catalyst to the promoter in the synthesis catalyst is in a range of 19 to 99. A ratio of aluminum phosphate to gamma alumina in the dehydration catalyst is in a range of 1:0.82 to 1:1.22. A mixing ratio of the methanol synthesis catalyst to the dehydration catalyst is in a range of 1:0.4 to 1:0.65.

According to another aspect of the present invention, there is provided a method producing a mixed catalyst used for producing dimethylether, comprising: steps of forming a methanol synthesis catalyst by mixing a metal nitrate solution with a sodium carbonate solution up to pH 7; forming a dehydration catalyst by mixing aluminum phosphate with gamma alumina; and mixing the methanol synthesis catalyst with the dehydration catalyst at a ratio of 1:0.4 to 1:0.65, wherein a ratio of the main catalyst to the promoter in the methanol synthesis catalyst is in a range of 19 to 99, and a ratio of aluminum phosphate to gamma alumina in the dehydration catalyst is in a range of 1:0.82 to 1:1.22.

According to still another aspect of the present invention, there is provided a method of producing dimethylether by reacting a synthesis gas containing hydrogen, carbon monoxide, and carbon dioxide at a reaction temperature of 200 to 350° C., a reaction pressure of 10 to 80 atm, and a space velocity (GHSV) of 3,000 to 10,000 $h^{-1}$ under the presence of the mixed catalyst.

BRIEF DESCRIPTION OF THE DRAWINGS

The above and other characteristics and advantages of the present invention will become more apparent by describing in detail exemplary embodiments thereof with reference to the attached drawings in which.

DETAILED DESCRIPTION OF THE INVENTION

Figure 1:
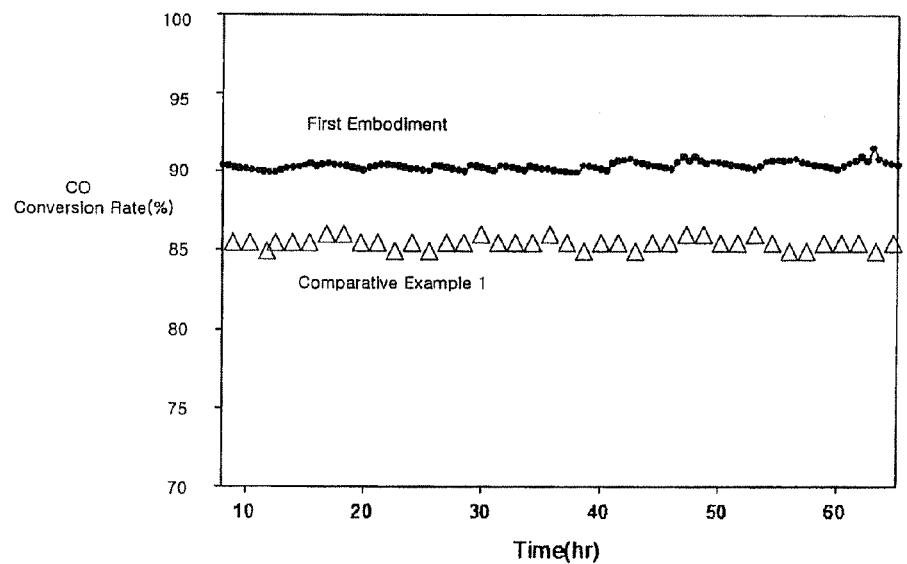
FIG. 1 is a graph showing a conversion rate of carbon monoxide according to time in production of dimethylether using a mixture catalyst according to the present invention and a catalyst according to Comparative Example 1.

Now, the present invention will be described in detail.

As mentioned above, according to the present invention, a mixed catalyst used for producing dimethylether includes the methanol synthesis catalyst and the dehydration catalyst.

The methanol synthesis catalyst includes a metal nitrate solution and a sodium carbonate solution.

The metal nitrate solution is formed by adding a promoter containing at least one selected from $Ca(NO_3)_2xH_2O$, $ZrO(NO_3)_2xH_2O$, $Ga(NO_3)_3xH_2O$, $Mg(NO_3)_2 6H_2O$ or $Cr(NO_3)_3 9H_2O$ to a main catalyst in which $Cu(NO_3)_2 3H_2O$, $Zn(NO_3)_2 6H_2O$, and $Al(NO_3)_3 9H_2O$ are mixed.

The dehydration catalyst is formed by mixing aluminum phosphate to gamma alumina.

It is preferable that the co-precipitation of the metal nitrate solution and the sodium carbonate solution used in order to produce the methanol synthesis catalyst is performed so that the final mixture is maintained at pH 7.

According to the present invention, it is preferable that the methanol synthesis catalyst and the dehydration catalyst are mixed so that the ratio of the methanol synthesis catalyst and the dehydration catalyst is in a range of 0.7/0.3 to 0.6/0.4 (that is, in a range of 1:0.4 to 1:0.65). Since an activity of the dehydration reaction of methanol depends on the quantity of acid sites, if the ratio is less than 0.3, strong solid acid sites exist, so that the activity is increased. Therefore, the dehydration reaction continues to proceed in dimethylether, so that a by-product such as hydrocarbon or coke is created. If the ratio exceeds 0.7, the activity of the dehydration reaction is decreased, so that it cannot function as a catalyst. Therefore, it is preferable that the methanol synthesis catalyst and the dehydration catalyst are mixed at a ratio of 1:0.4 to 1:0.65 in terms of the selectivity and the conversion rate. In addition, it is preferable that a ratio of aluminum phosphate to gamma alumina in the dehydration catalyst is in a range of 0.45/0.55 to 0.55/0.45 (that is, in a range of 1:0.82 to 1:1.22) in terms of the selectivity and the conversion rate.

Meanwhile, it is preferable that the reaction temperature for producing dimethylether from the synthesis gas containing hydrogen, carbon monoxide, and carbon dioxide by using the mixed catalyst is in a range of 200 to 350° C., the reaction pressure is in a range of 10 to 80 atm, and the space velocity (GHSV) is in a range of 3,000 to 10,000 $h^{-1}$. If the reaction temperature is less than 200° C., the conversion rate is lowered. If the reaction temperature exceeds 350° C., the selectivity deteriorates.

Moreover, the reaction pressure of less than 10 atm is unfavorable thermodynamically for a production of dimethylether. The reaction pressure exceeding 80 atm is not suitable due to problems in reaction operation. If the space velocity of the mixed gas is less than 3,000 $h^{-1}$, the reaction productively is too lowered. If the space velocity exceeds 10,000 $h^{-1}$, the contact time with respect to the catalyst becomes short, so that the conversion rate is lowered.

A fluidized bed reactor or a fixed bed reactor in gas phase can be used as the reactor. The same effect can be obtained by using any one of the reactors.

Now, although the present invention will be described in more detail through exemplary embodiments, the scope of the present invention is not limited thereto.

First Embodiment

The mixed catalyst was produced as follows. The methanol synthesis catalyst and the dehydration catalyst are separated formed, and these catalystis are mixed physically. The methanol synthesis catalyst was formed by dissolving 18.22 g $Cu(NO_3)_2 3H_2O$, 21.9 g $Zn(NO_3)_2 6H_2O$, 10.49 g $Al(NO_3)_3 9H_2O$, and 0.44 g $Ca(NO_3)_2 xH_2O$ in 200 ml distilled water in order to obtain a metal nitrate solution. A sodium carbonate solution was formed by dissolving 60 g $Na_2CO_3$ in 400 ml distilled water. The metal nitrate solution and the sodium carbonate solution were dropped and mixed over 300 ml water to be pH 7. After precipitation, sludge thereof is filtered and washed with distilled water 3 times. The sludge was dried at 120° C. and calcined in air at 350 to 380° C. for 4 to 5 hours. As a result, a $CuO/ZnO/CaO/Al_2O_3$ catalyst was obtained.

The dehydration catalyst was formed by dissolving 150 g $Al(NO_3)_3 9H_2O$ in 375 ml distilled water, adding 15.37 g $H_3PO_4$ (85%) to the aqueous solution, thereby obtaining an aluminum phosphate solution. The aluminum phosphate solution was titrated by a precipitant produced by dissolving 70.87 g 28% $NH_4OH$ into 500 ml distilled water with keeping pH 9. Then, the resulting sludge was filtered, washed with distilled water 3 times, so that the sludge was obtained. The sludge was dried at 120° C. for 5 hours and calcined in air at 500° C. for 4 to 5 hours. Thus, aluminum phosphate was obtained. The resulting aluminum phosphate was mixed with gamma alumina of which a specific surface area is more than 260 m² in a ratio of 50:50 to obtain the dehydration reaction catalyst.

The mixed catalyst used for producing dimethylether was formed by mixing the methanol synthesis catalyst with the dehydration catalyst uniformly in the powder state in a ratio of 60:40 to 70:30. And 0.6 g catalyst thereof was filled in a fixed bed reactor. Under the this condition, a mixed gas containing 10% hydrogen and 90% nitrogen flowed at a flow velocity of 50 ml/minute to carry out pretreatment for reduction of the mixed catalyst at 300° C. The reaction of producing dimethylether was performed so that mixed gas of carbon monoxide and hydrogen (a 1:1 volume ratio of $H_2$:CO) was arranged to pass through the mixed catalyst layer in the condition of 60 atm and 280° C. at a space velocity of 4,000 $h^{-1}$. The reaction results are shown in Table 1.

Second Embodiment

Procedures same as those of the first embodiment were employed to produce the mixed catalyst, except that the methanol synthesis catalyst was formed by dissolving 18.22 g $Cu(NO_3)_2 3H_2O$, 21.9 g $Zn(NO_3)_2 6H_2O$, 10.49 g $Al(NO_3)_3 9H_2O$, and 0.28g $ZrO(NO_3)_2 xH_2O$ in 200 ml distilled water in order to obtain a metal nitrate solution. The sodium carbonate solution was formed by dissolving 60 g $Na_2CO_3$ in 400 ml distilled water. The metal nitrate solution and the sodium carbonate solution were dropped and mixed over 300 ml water to be pH 7. After precipitation, sludge thereof is filtered and washed with distilled water 3 times. The sludge was dried at 120° C. and calcined in air at 380° C. for 4 to 5 hours. Thus, a $CuO/ZnO/ZrO_2/Al_2O_3$ catalyst was obtained.

Procedures same as those of the first embodiment were employed to produce the dehydration catalyst. The mixing ratio in the mixed catalyst used for producing dimethylether (DME) was the same as that of the first embodiment. The reaction results are shown in Table 1.

Third Embodiment

Procedures same as those of the first embodiment were employed to produce the mixed catalyst, except that the methanol synthesis catalyst was formed by dissolving 18.22 g $Cu(NO_3)_2 3H_2O$, 21.9 g $Zn(NO_3)_2 6H_2O$, 10.38 g $Al(NO_3)_3 9H_2O$, and 0.95 g $Mg(NO_3)_2 6H_2O$ in 200 ml distilled water in order to obtain a metal nitrate solution. The sodium carbonate solution was formed by dissolving 60 g $Na_2CO_3$ in 400 ml distilled water. The metal nitrate solution and the sodium carbonate solution were dropped and mixed over 300 ml water to be pH 7. After precipitation, sludge thereof is filtered and washed with distilled water 3 times. The sludge was dried at 120° C. and calcined in air at 380° C. for 4 to 5 hours. Thus, a $CuO/ZnO/MgO/Al_2O_3$ catalyst was obtained.

Procedures same as those of the first embodiment were employed to produce the dehydration catalyst. The mixing ratio in the mixed catalyst used for producing dimethylether (DME) was the same as that of the first embodiment. The reaction results are shown in Table 1.

Fourth Embodiment 4

Procedures same as those of the first embodiment were employed to produce the mixed catalyst, except that the methanol synthesis catalyst was formed by dissolving 18.22 g $Cu(NO_3)_2 3H_2O$, 21.9 g $Zn(NO_3)_2 6H_2O$, 10.49 g $Al(NO_3)_3 9H_2O$, and 0.21 g $Ga(NO_3)_3 xH_2O$ in 200 ml distilled water in order to obtain a metal nitrate solution. The sodium carbonate solution was formed by dissolving 60 g $Na_2CO_3$ in 400 ml distilled water. The metal nitrate solution and the sodium carbonate solution were dropped and mixed over 300 ml water to be pH 7. After precipitation, sludge thereof is filtered and washed with distilled water 3 times. The sludge was dried at 100 to 120° C. and calcined in air at 380° C. for 4 to 5 hours. Thus, a $CuO/ZnO/Ga_2O_3/Al_2O_3$ catalyst was obtained.

Procedures same as those of the first embodiment were employed to produce the dehydration catalyst. The mixing ratio in the mixed catalyst used for producing dimethylether (DME) was the same as that of the first embodiment. The reaction results are shown in Table 1.

Fifth Embodiment

Procedures same as those of the first embodiment were employed to produce the mixed catalyst, except that the methanol synthesis catalyst was formed by dissolving 18.22 g $Cu(NO_3)_2 3H_2O$, 21.9 g $Zn(NO_3)_2 6H_2O$, 9.93 g $Al(NO_3)_3 9H_2O$, 0.28 g $ZrO(NO_3)_2 xH_2O$, and 0.44 g $Ca(NO_3)_2 xH_2O$ in 200 ml distilled water in order to obtain a metal nitrate solution. The sodium carbonate solution was formed by dissolving 60 g $Na_2CO_3$ in 400 ml distilled water. The metal nitrate solution and the sodium carbonate solution were dropped and mixed over 300 ml water to be pH 7. After precipitation, sludge thereof is filtered and washed with distilled water 3 times. The sludge was dried at 120° C and calcined in air at 380° C. for 4 to 5 hours. Thus, a $CuO/ZnO/CaO/ZrO_2/Al_2O_3$ catalyst was obtained.

Procedures same as those of the first embodiment were employed to produce the dehydration catalyst. The mixing ratio in the mixed catalyst used for producing dimethylether (DME) was the same as that of the first embodiment. The reaction results are shown in Table 1.

Sixth Embodiment

Procedures same as those of the first embodiment were employed to produce the mixed catalyst, except that the methanol synthesis catalyst was formed by dissolving 18.22 g $Cu(NO_3)_2 3H_2O$, 21.9 g $Zn(NO_3)_2 6H_2O$, 9.93 g $Al(NO_3)_3 9H_2O$, 0.21 g $Ga(NO_3)_3 xH_2O$, and 0.28 g $ZrO(NO_3)_2 xH_2O$ in 200 ml distilled water in order to obtain a metal nitrate solution. The sodium carbonate solution was formed by dissolving 60 g $Na_2CO_3$ in 400 ml distilled water. The metal nitrate solution and the sodium carbonate solution were dropped and mixed over 300 ml water to be pH 7. After precipitation, sludge thereof is filtered and washed with distilled water 3 times. The sludge was dried at 120° C. and calcined in air at 380° C. for 4 to 5 hours. Thus, a CuO/ZnO/Ga$_2$O$_3$/ZrO$_2$/Al$_2$O$_3$ catalyst was obtained.

Procedures same as those of the first embodiment were employed to produce the dehydration catalyst. The mixing ratio in the mixed catalyst used for producing dimethylether (DME) was the same as that of the first embodiment. The reaction results are shown in Table 1.

Seventh Embodiment

Procedures same as those of the first embodiment were employed to produce the mixed catalyst, except that the methanol synthesis catalyst was formed by dissolving 18.22 g Cu(NO$_3$)$_2$3H$_2$O, 21.9 g Zn(NO$_3$)$_2$6H$_2$O, 9.93 g Al(NO$_3$)$_3$9H$_2$O, 0.21 g Ga(NO$_3$)$_3$xH$_2$O, and 0.95 g Mg(NO$_3$)$_2$6H$_2$O in 200 ml distilled water in order to obtain a metal nitrate solution. The sodium carbonate solution was formed by dissolving 60 g Na$_2$CO$_3$ in 400 ml distilled water. The metal nitrate solution and the sodium carbonate solution were dropped and mixed over 300 ml water to be pH 7. After precipitation, sludge thereof is filtered and washed with distilled water 3 times. The sludge was dried at 120° C. and calcined in air at 380° C. for 4 to 5 hours. Thus, a CuO/ZnO/MgO/Ga$_2$O$_3$/Al$_2$O$_3$ catalyst was obtained.

Procedures same as those of the first embodiment were employed to produce the dehydration catalyst. The mixing ratio in the mixed catalyst used for producing dimethylether (DME) was the same as that of the first embodiment. The reaction results are shown in Table 1.

COMPARATIVE EXAMPLE 1

Procedures same as those of the first embodiment were employed to produce the mixed catalyst, except that the methanol synthesis catalyst was formed by dissolving 18.22 g Cu(NO$_3$)$_2$3H$_2$O, 21.9 g Zn(NO$_3$)$_2$6H$_2$O, and 11.94 g Al(NO$_3$)$_3$9H$_2$O in 200 ml distilled water in order to obtain a metal nitrate solution. The sodium carbonate solution was formed by dissolving 60 g Na$_2$CO$_3$ in 400 ml distilled water. The metal nitrate solution and the sodium carbonate solution were dropped and mixed over 300 ml water to be pH 7. After precipitation, sludge thereof is filtered and washed with distilled water 3 times. The sludge was dried at 120° C. and calcined in air at 380° C. for 4 to 5 hours. Thus, a CuO/ZnO/Al$_2$O$_3$ catalyst was obtained.

Procedures same as those of the first embodiment were employed to produce the dehydration catalyst. The mixing ratio in the mixed catalyst used for producing dimethylether (DME) was the same as that of the first embodiment. The reaction results are shown in Table 1.

TABLE 1

| classification | Conversion rate of Carbon monoxide (%) | Selectivity of Dimethylether (%) |
| --- | --- | --- |
| First Embodiment | 85.80 | 65.25 |
| Second Embodiment | 83.55 | 64.76 |
| Third Embodiment | 84.09 | 52.77 |
| Fourth Embodiment | 84.31 | 65.35 |
| Fifth Embodiment | 81.38 | 64.80 |
| Sixth Embodiment | 91.79 | 64.01 |
| Seventh Embodiment | 86.12 | 65.28 |
| Comparative Example 1 | 81.20 | 60.58 |

The Table 1 above shows the reaction results of the first to seventh embodiments and Comparative Example 1. According to the reaction results in the embodiments of the present invention and Comparative Example 1, one or more metal components selected from components of the mixed catalyst which is used to produce the dimethylether from the synthesis gas containing hydrogen, carbon monoxide, and carbon dioxide is used as a promoter. When the reaction is carried out under a given reaction temperature, a given reaction pressure and a given space velocity, a high conversion rate of carbon monoxide can be obtained, and dimethylether can be produced selectively.

Figure 2:
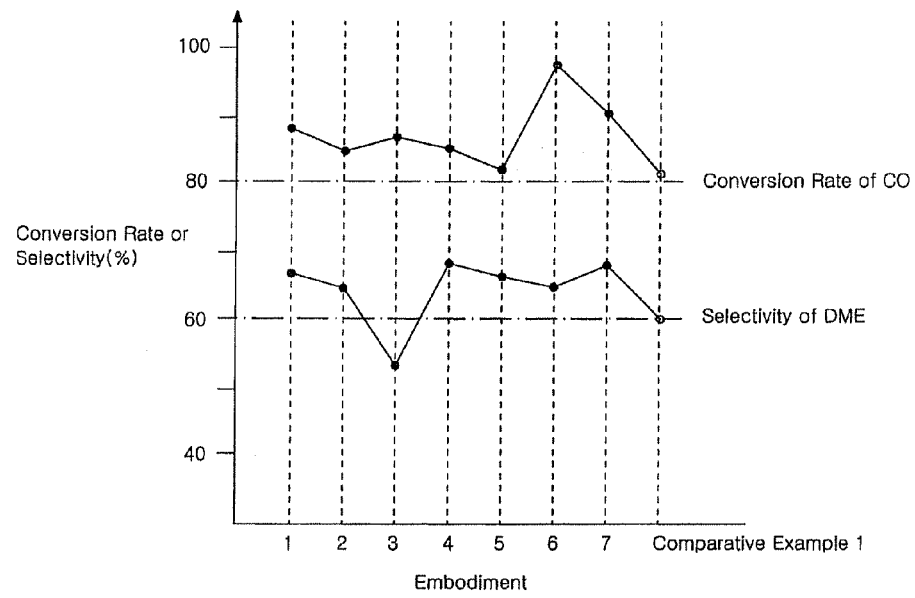
FIG. 2 is a graph showing a conversion rate of carbon monoxide and a selectivity of dimethylether in production of dimethylether using the mixture catalyst according to the present invention and the catalyst according to Comparative Example 1.

FIGS. 1 and 2 illustrates changes of a stability of catalysts and a conversion rate of carbon monoxide and a selectivity of dimethylether in order to compare catalysts produced according to the embodiments of the present invention and Comparative Example 1.

Referring to FIG. 1, it can be seen that in case of using a mixed catalyst added with a promoter according to the first embodiment of the present invention, a high conversion rate of carbon monoxide can be maintained for a long time in comparison with Comparative Example 1 of using a mixed catalyst without the added promoter.

Referring to FIG. 2, it can be seen that in case of using a mixed catalyst added the promoter according to the first to seventh embodiments of the present invention, a high conversion rate of carbon monoxide and a high selectivity of dimethylether can be obtained in comparison with Comparative Example 1 of using the mixed catalyst without the added promoter.

As mentioned above, when dimethylether is produced from a synthesis gas containing hydrogen, carbon monoxide, and carbon dioxide by using a mixed catalyst used for producing dimethylether according to the present invention, a high conversion rate of carbon monoxide can be maintained, and dimethylether can be produced selectively for a certain time from an initial reaction. Therefore, this method is expected to be practicable to industries in the future.

What is claimed is:

1. A mixed catalyst used for producing dimethylether comprising:
    a methanol synthesis catalyst produced from a sodium carbonate solution and a metal nitrate solution formed by adding a promoter including at least one selected from Mg, Zr, Ga, Ca, or the oxide thereof to a main catalyst comprised of a copper nitrate solution, a zinc nitrate solution, and an aluminum nitrate solution; and
    a dehydration catalyst formed by mixing aluminum phosphate (AlPO$_4$) with gamma alumina,
    wherein a ratio of the main catalyst to the promoter in the methanol synthesis catalyst is in a range of 19 to 99,
    wherein a ratio of aluminum phosphate to gamma alumina in the dehydration catalyst is in a range of 1:0.82 to 1:1.22, and
    wherein a mixing ratio of the methanol synthesis catalyst to the dehydration catalyst is in a range of 1:0.4 to 1:0.65.

2. The mixed catalyst according to claim 1, wherein the main catalyst comprises Cu(NO$_3$)$_2$3H$_2$O, Zn(NO$_3$)$_2$6H$_2$O, and Al(NO$_3$)$_3$9H$_2$O;

3. A method of producing a mixed catalyst used for producing dimethylether, comprising steps of:
    producing a methanol synthesis catalyst by mixing a metal nitrate solution with a sodium carbonate solution up to pH 7, wherein the metal nitrate solution is formed by adding a promoter including at least one selected from Mg, Zr, Ga, Ca, or the oxide thereof to a main catalyst comprised of Cu(NO$_3$)$_2$3H$_2$O, Zn(NO$_3$)$_2$6H$_2$O, and Al(NO$_3$)$_3$9H$_2$O;
    producing a dehydration catalyst by mixing aluminum phosphate with gamma alumina; and
    mixing the methanol synthesis catalyst with the dehydration catalyst at a ratio of between 1:0.4 and 1:0.65, wherein a ratio of the main catalyst to the promoter in the methanol synthesis catalyst is in a range of 19 to 99, and a ratio of aluminum phosphate to gamma alumina in the dehydration catalyst is in a range of 1:0.82 to 1:1.22.

4. A method of producing dimethylether, by reacting the synthesis containing hydrogen, carbon monoxide, and carbon dioxide at a reaction temperature of 200 to 350° C., a reaction pressure of 10 to 80 atm, and a space velocity(GHSV) of 3,000 to 10,000 $h^{-1}$ under the presence of the mixed catalyst according to claim 1.

5. The method according to claim 4, wherein the reaction is performed in a fluidized bed reactor or in a fixed bed reactor in gas phase.

\* \* \* \* \*